(12) United States Patent
Dishon

(10) Patent No.: US 9,439,741 B2
(45) Date of Patent: Sep. 13, 2016

(54) REPLACEMENT BRUSH HEAD FOR AN ELECTRIC TOOTHBRUSH

(71) Applicant: Ranir, LLC, Grand Rapids, MI (US)

(72) Inventor: Bryan J. Dishon, Grand Rapids, MI (US)

(73) Assignee: Ranir, LLC, Grand Rapids, MI (US)

( * ) Notice: Subject to any disclaimer, the term of this patent is extended or adjusted under 35 U.S.C. 154(b) by 336 days.

(21) Appl. No.: 14/212,020

(22) Filed: Mar. 14, 2014

(65) Prior Publication Data

US 2015/0257862 A1    Sep. 17, 2015

(51) Int. Cl.
A61C 17/22    (2006.01)
A61C 17/34    (2006.01)

(52) U.S. Cl.
CPC ......... A61C 17/222 (2013.01); A61C 17/3436 (2013.01)

(58) Field of Classification Search
CPC   A61C 17/222; A61C 17/3436; A61C 17/26; A46B 13/02
See application file for complete search history.

(56) References Cited

U.S. PATENT DOCUMENTS

| | | | |
|---|---|---|---|
| 5,577,285 A | 11/1996 | Drossler | |
| 6,195,828 B1 | 3/2001 | Fritsch | |
| 6,308,359 B2 | 10/2001 | Fritsch et al. | |
| 6,367,108 B1* | 4/2002 | Fritsch | A61C 17/22 |
| | | | 15/22.1 |
| 6,511,319 B1 | 1/2003 | Hunter | |
| 6,588,042 B2 | 7/2003 | Fritsch et al. | |
| 8,631,532 B2* | 1/2014 | Utsch | A61C 17/3436 |
| | | | 15/22.1 |
| 9,003,590 B2* | 4/2015 | Utsch | A61C 17/222 |
| | | | 15/22.1 |
| 9,226,808 B2* | 1/2016 | Utsch | A61C 17/222 |
| 2003/0019057 A1* | 1/2003 | Dickie | A61C 17/34 |
| | | | 15/22.1 |
| 2012/0060309 A1 | 3/2012 | Kressner | |
| 2013/0029289 A1* | 1/2013 | Utsch | A61C 17/222 |
| | | | 433/146 |
| 2013/0029290 A1* | 1/2013 | Utsch | A61C 17/3436 |
| | | | 433/147 |
| 2013/0134062 A1 | 5/2013 | Sauer et al. | |
| 2013/0180063 A1 | 7/2013 | Reinbold | |
| 2014/0026337 A1* | 1/2014 | Utsch | A61C 17/222 |
| | | | 15/22.1 |

FOREIGN PATENT DOCUMENTS

| | | |
|---|---|---|
| DE | 202008005856 | 9/2008 |
| WO | 2004098444 | 11/2004 |
| WO | 2004098445 | 11/2004 |

OTHER PUBLICATIONS

European Search Report dated Aug. 7, 2015, International Application No. EP 15 15 2160.

* cited by examiner

*Primary Examiner* — Dung Van Nguyen

(74) *Attorney, Agent, or Firm* — Warner Norcross & Judd LLP

(57) ABSTRACT

A replacement head for an electric toothbrush has a simplified drive construction and desired bristle carrier retention. The replacement head includes a tubular neck with a head at one end and a brush shaft disposed within the neck. An eccentric extension extends from the brush shaft parallel with the longitudinal axis and an axial extension extends parallel to the eccentric extension. The eccentric extension engages the bristle carrier to drive the bristle carrier. The brush shaft, including the eccentric extension and the axial extension, may be formed together as a single unitary piece. A pin may extend through pin retention openings in the head and a pin slot in the bristle carrier in a direction transverse to both the longitudinal axis and the carrier rotation axis to retain the bristle carrier on the head.

18 Claims, 12 Drawing Sheets

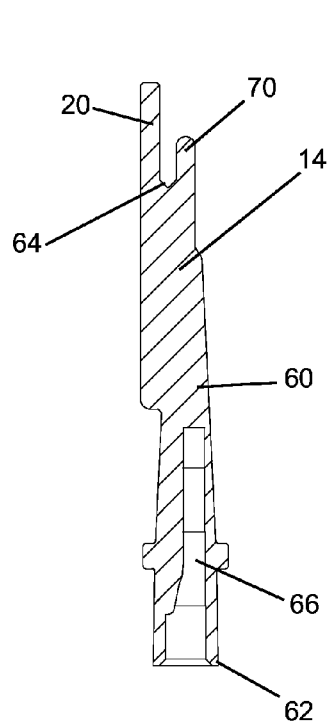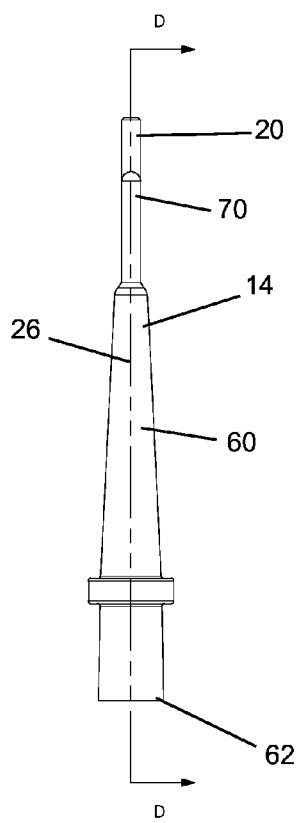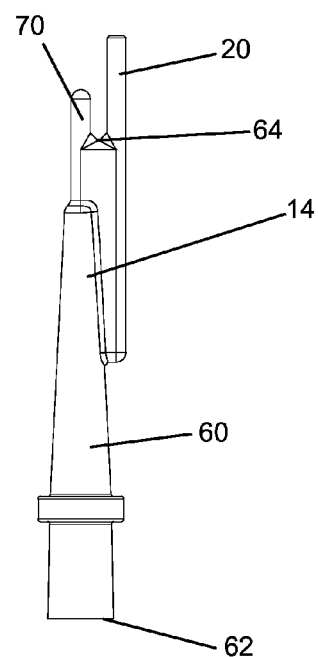
Fig. 6
Fig. 7
Fig. 5

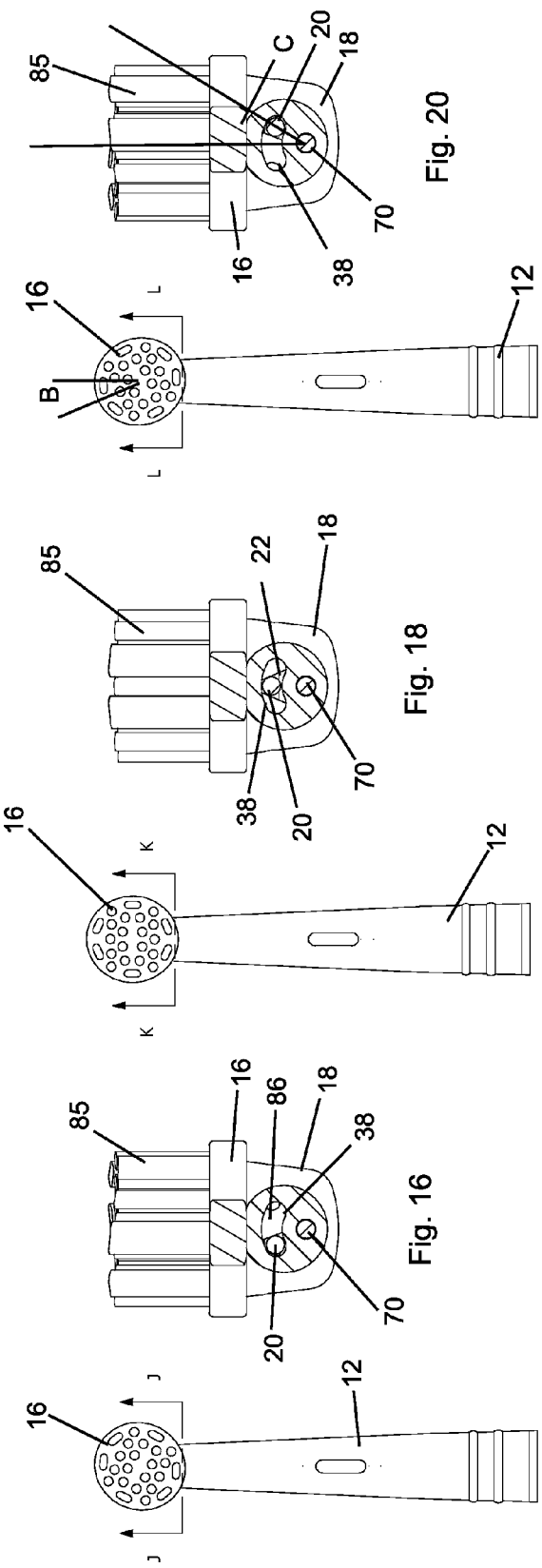

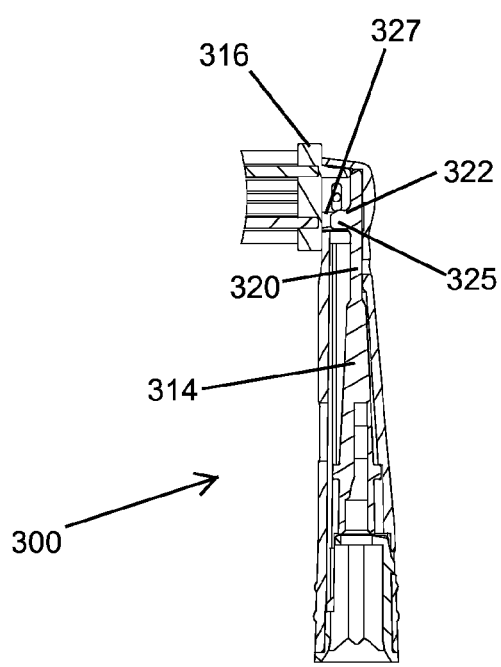
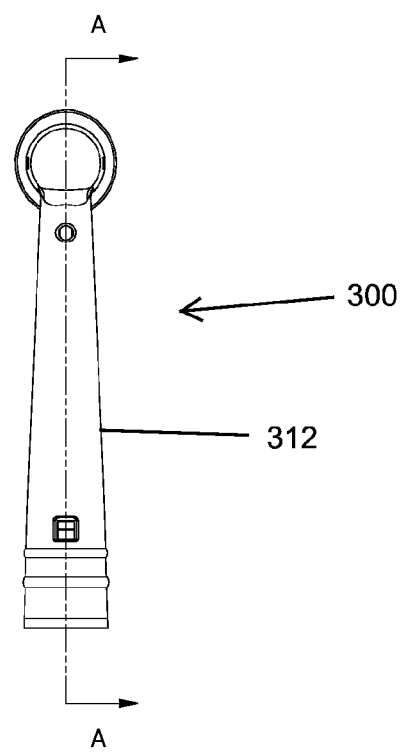
Fig. 26
Fig. 25

REPLACEMENT BRUSH HEAD FOR AN ELECTRIC TOOTHBRUSH

BACKGROUND OF THE INVENTION

The present invention is directed to electric toothbrushes, and, more particularly, to a replacement head that is attachable to an electric toothbrush drive unit.

Recognizing that toothbrush bristles require periodic replacement, manufacturers have designed replacement heads to fit onto separate drive units of electric toothbrushes. The drive units typically include a power source, switch and a drive shaft. The replacement heads typically can be removably attached to the drive units by threading or snap-fitting a portion of the replacement head onto a portion of the drive unit.

Replacement heads typically include an elongated neck with an internal brush shaft connected to a bristle bearing head. The brush shaft is arranged to transfer power from the drive shaft to the brush head for moving the brush head in a desired manner. Many brush heads are configured to convert rotational or oscillatory movement of the drive shaft about a longitudinal axis into rotational or oscillatory movement of the bristle head about an axis that is perpendicular to the longitudinal axis of the drive shaft. A variety of brush head configurations are known for providing this conversion. These brush heads commonly include multiple internal components for driving the bristle carrier and converting the motion. For example, a brush head may include a brush shaft extending within a hollow neck, a first separate drive element attached to the brush shaft aligned with the longitudinal axis of the brush head, and a second separate drive element attached to the brush shaft and offset from the longitudinal axis. One of the drive elements is connected to a bristle carrier by a gear or linkage to drive the brush head in a desired direction. Manufacturing and assembling these components can be time consuming and costly, and can lead to unwanted squeaking and rattling during operation.

Additional problems may arise with the retention of the bristle carrier on the brush head. Because the bristle carrier must be mounted for rotation and also be linked to the brush shaft to receive motion from the brush shaft, the space for structure to retain the bristle carrier on the brush head is limited. This can lead to unwanted gaps between the carrier and head, and in some cases unwanted separation of the bristle carrier.

SUMMARY OF THE INVENTION

The present invention provides a replacement head for an electric toothbrush with a simplified drive construction and desired bristle carrier retention. In one embodiment, the replacement head includes a tubular neck with a head at one end. A brush shaft is disposed within the tubular neck. The brush shaft defines a longitudinal axis and includes a shaft end and a head end opposite the shaft end. An eccentric extension extends from the head end parallel with the longitudinal axis and an axial extension extends from the head end parallel to the eccentric extension. The eccentric extension engages the bristle carrier to drive the bristle carrier. The brush shaft, including the eccentric extension and the axial extension, may be formed together as a single unitary piece.

In one embodiment, the neck defines an arcuate slot extending from the tubular opening into the head. The eccentric extension extends through the slot and into the head to engage the bristle carrier. Rotary oscillation of the brush shaft about the longitudinal axis drives the bristle carrier to rotate about a carrier axis perpendicular to the longitudinal axis. The bristle carrier may include an angled opening for receiving the eccentric extension. The angled opening may be V-shaped. The angle of the V-shaped opening, the size of the eccentric extension, and the size of the arcuate slot may be controlled to provide the bristle carrier with a desired range of motion about the carrier axis.

In another embodiment, the head includes an upwardly opening sidewall defining a pair of opposing pin retention openings. The bristle carrier defines a pin slot extending generally perpendicular to the angled opening. A pin extends through the pin retention openings and the pin slot in a direction transverse to both the longitudinal axis and the carrier axis to retain the bristle carrier on the head. The pin slot may have a width greater than the diameter of the pin to allow movement of the bristle carrier with respect to the pin. The bristle carrier may thus be rotationally supported by the pin without engagement with the floor of the head.

The brush shaft design of the present invention provides a simplified drive construction that is desirable for manufacture and assembly, while also providing controlled movement of the bristle carrier. The pin supports the bristle carrier for rotation, and may enhance the retention strength of the bristle carrier.

BRIEF DESCRIPTION OF THE DRAWINGS

FIG. 5 is a bottom view of a brush shaft according to one embodiment.

FIG. 6 is a side cross-sectional view taken along line D-D in FIG. 5.

FIG. 7 is a side view thereof.

FIG. 15 is a top view of a brush head showing the bristle carrier displaced to a first angular position.

FIG. 16 is a rear cross-sectional view thereof taken along line J-J in FIG. 15.

FIG. 17 is a top view of a brush head with the bristle carrier in a central position.

FIG. 18 is a rear cross-sectional view thereof taken along line K-K in FIG. 17.

FIG. 19 is a top view of a brush head showing the bristle carrier displaced to a third angular position.

FIG. 20 is a rear cross-sectional view thereof taken along line L-L in FIG. 19.

FIG. 25 is a rear view thereof.

FIG. 26 is a side cross-sectional view taken along line A-A in FIG. 25.

Figure 1:
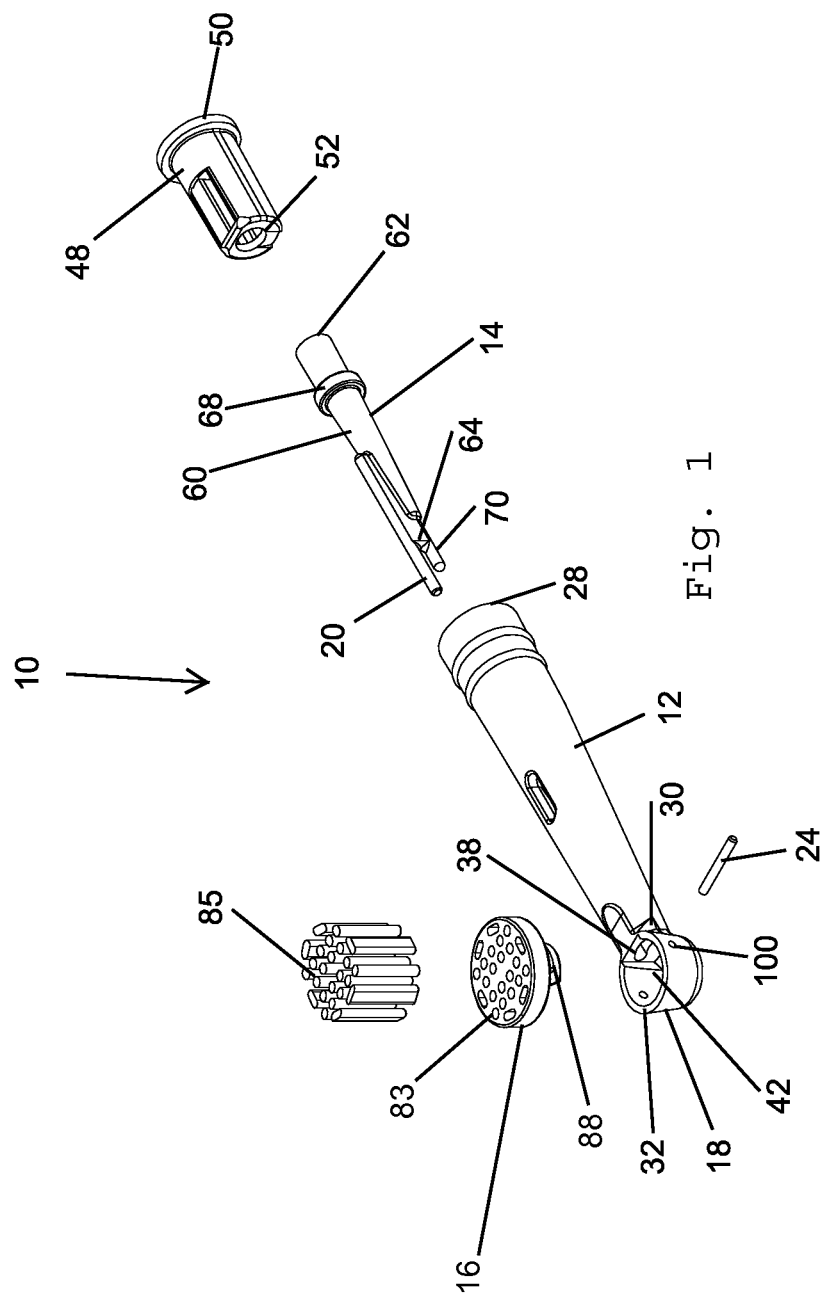
FIG. 1 is an exploded view of a brush head according to one embodiment of the present invention.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and may be practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENTS

A. Overview

A replacement head for an electric toothbrush according to one embodiment of the present invention is shown in FIG. 1 and generally designated 10. The brush head 10 generally includes a hollow neck portion 12, a brush shaft 14 disposed within the hollow interior of the neck portion 12, and a bristle carrier 16 disposed on a head 18 at one end of the neck 12.

The brush head 10 of the illustrated embodiment may be secured to a drive unit, with a drive shaft interfitted with one end of the brush shaft 14. Rotary oscillation of the drive shaft about a longitudinal axis produces rotary oscillation of the brush shaft 14 about the same axis 26. An eccentric extension 20 on the brush shaft 14 may extend into an angled opening 22 in the bristle carrier 16, such that movement of the eccentric extension 20 within the angled opening 22 causes rotation of the bristle carrier 16 about a carrier axis that is transverse to the longitudinal axis of the brush shaft 14. More particularly, the eccentric extension 20 may be formed with the brush shaft 14 as a single unitary piece. A retention pin 24 may extend through the head 18 and the bristle carrier 16 in a direction transverse to both the longitudinal axis 26 of the brush shaft 14 and the carrier axis. The retention pin 24 may retain the bristle carrier 16 on the head 18, while enabling rotation of the bristle carrier 16 about the carrier axis.

B. Structure

As shown, the replacement brush head 10 includes a neck 12. The neck 12 may be a generally tubular hollow body that extends along a longitudinal axis 26. In one embodiment, the neck includes an open proximal end 28 and an opposite distal end 30. The head 18 extends from the distal end 30. As illustrated, the head is a generally cylindrical portion having an upper rim 32 defining an opening, and a floor 34. The neck 12 and head 18 may be formed as a single piece, for instance, by molding from a known plastic such as polyoxymethylene (POM), polyvinylchloride (PVC), acrylonitrile butadiene styrene (ABS), or another known plastic. The plastic material is provided with a desired hardness suited to maintain form during use while providing a degree of flexibility for user comfort and an effective friction fit with the toothbrush handle. In one embodiment, the plastic material has a hardness of between about 50 and 100 Shore A durometer to meet the desired characteristics. In another embodiment, the plastic material has between about 75 and 90 Shore A durometer, and in a more particular embodiment the plastic has a hardness of about 86 Shore A durometer.

Figures 2, 3:
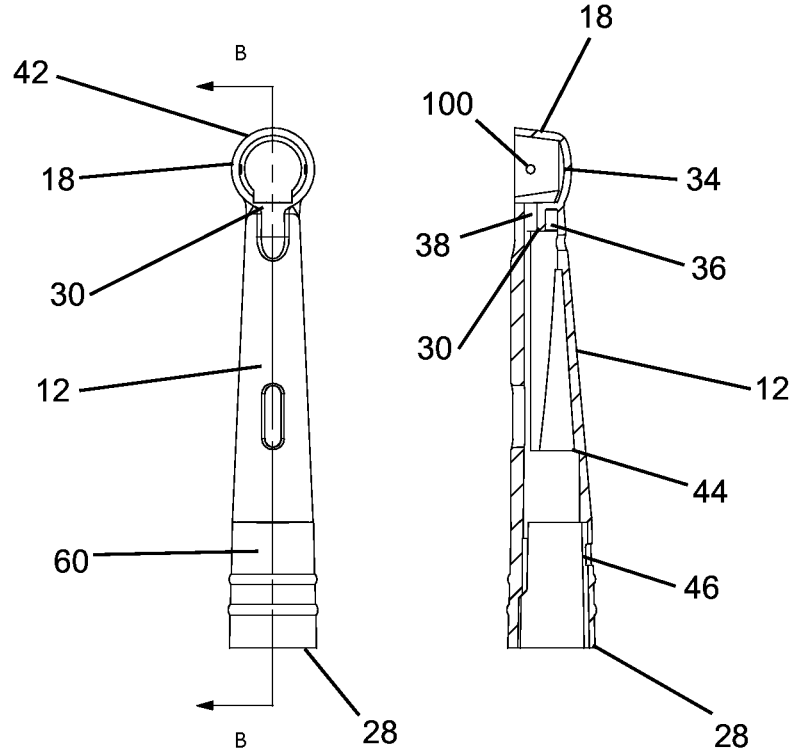
FIG. 2 is a top view thereof.
FIG. 3 is a side cross-sectional view taken along line B-B in FIG. 2.
Figure 4D:
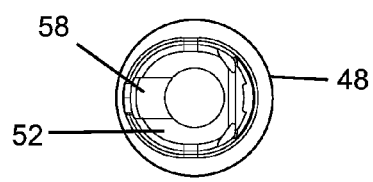
FIG. 4d is a top view of the sleeve.
Figure 4:
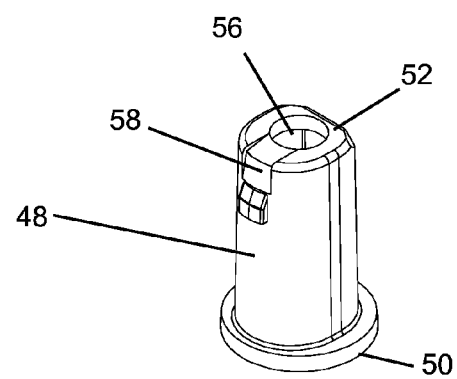
FIG. 4 is a perspective view of a sleeve according to one embodiment.
Figure 4B:
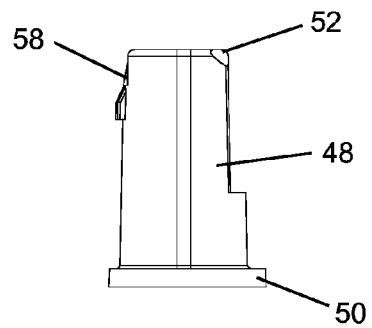
FIG. 4b is a side view of the sleeve.
Figure 4C:
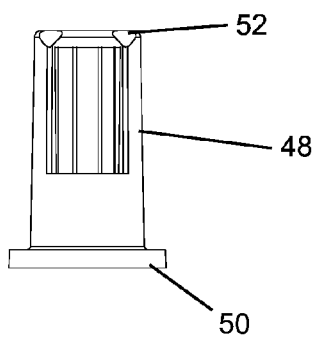
FIG. 4c is a front view of the sleeve.
Figure 4A:
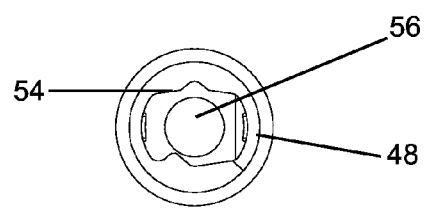
FIG. 4a is a rear view of the sleeve.

The interior of the tubular neck 12 may include structure for receiving, retaining and guiding the brush shaft 14 when the brush shaft is disposed within the neck 12. Referring to FIG. 3, the distal end 30 of the neck 12 may define an axial receptacle 36 and an arcuate slot 38. In one embodiment, the axial receptacle 36 is a generally cylindrical opening that may be aligned along the longitudinal axis of the brush shaft 14. The arcuate slot 38 may be offset from the longitudinal axis of the brush shaft 14 by a desired distance and may extend completely through the distal end 30 of the neck 12 such that it opens into the head opening 42. The internal surface of the neck may further include a ledge forming a bearing surface 44 for interfitting with the brush shaft 14 as described below. Additionally, the proximal end 28 of the neck 12 may include structure for mounting to the handle of a drive unit. In the case of the illustrated embodiment, the proximal end 28 includes structure for receiving a sleeve 48 that may be inserted into the proximal end 28 to assist in mounting the brush head 10 to the drive unit. In particular, the proximal end 28 of the neck 12 may include a detent 46 for retaining the sleeve 48. Shown more particularly in FIGS. 4-4d, the sleeve 48 includes a handle end 50 and a second end 52 opposite the handle end 50. The sleeve 48 may include mounting structure 54 configured to receive a portion of the toothbrush drive unit and to prevent unwanted rotation between the brush head 10 and the drive unit. The sleeve 48 defines a central opening 56 extending generally along the longitudinal axis 26 of the brush shaft 14, and a catch opening 58 that may receive the detent 46 on the neck 12 to retain the sleeve 48 within the neck 12 and prevent rotation of the sleeve 48 with respect to the neck 12. In an alternative embodiment, the brush head 10 may not include a sleeve 48, and may include mounting structure for mounting to the drive unit within the proximal end 28 of the neck 12.

Figure 14:
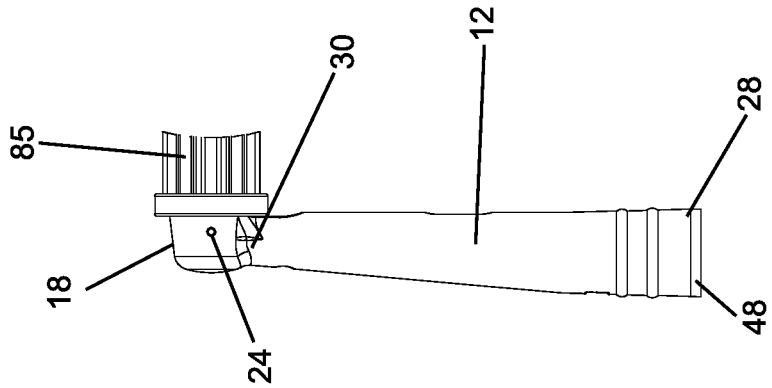
FIG. 14 is a side cross-sectional view taken along line A-A in FIG. 12.
Figure 12:
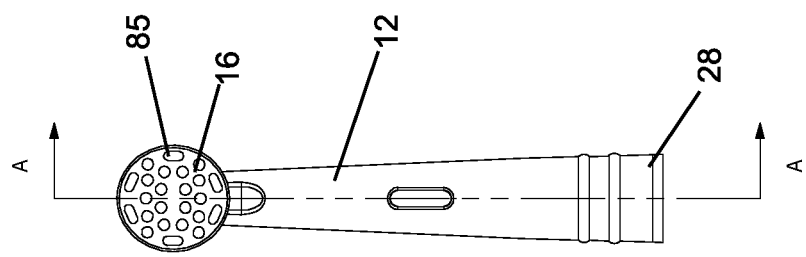
FIG. 12 is a top view of a brush head according to one embodiment.
Figure 13:
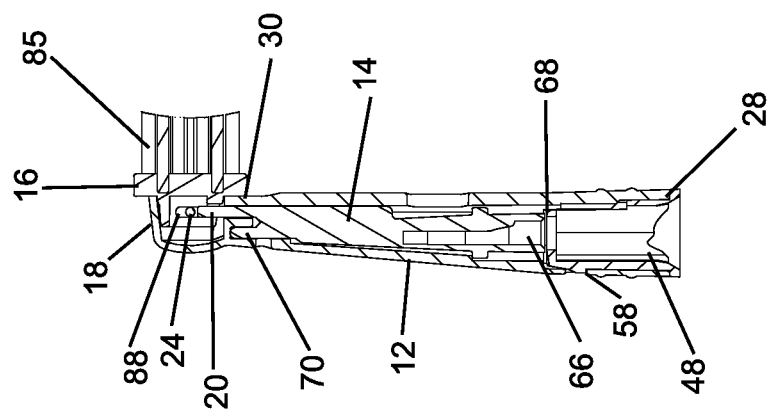
FIG. 13 is a side view thereof.

FIGS. 5, 6 and 7 show details of the brush shaft 14 to be inserted into the neck 12. As illustrated, the brush shaft 14 includes a main body 60 having a shaft end 62 and a head end 64 opposite the shaft end 62. In the illustrated embodiment, the main body 60 has a generally conical shape that tapers in diameter from the shaft end 62 to the head end 64. The shaft end 62 may define an opening 66 shaped to receive the tip of a drive shaft. An annular ring 68 may be disposed about the exterior of the main body 60. As illustrated, the ring 68 extends completely around the circumference of the main body 60 and protrudes outwardly from the main body 60. The head end 64 of the main body 60 includes an axial extension 70 and the eccentric extension 20. The axial extension 70 may be generally cylindrical and may be sized to fit snugly within the axial receptacle 36 at the distal end of the neck 12, wherein the axial extension 70 is capable of rotation about the longitudinal axis within the axial receptacle 36. The eccentric extension 20 extends from the head end 64 at an offset from the axial extension 70. The amount of the offset may be varied as desired to control the amount of angular movement of the eccentric extension 20 and thus the distance of travel of the bristle carrier 16 during operation. In the illustrated embodiment, the eccentric extension 20 extends from the head end 64 a greater distance than the axial extension 70 such that the tip of the eccentric extension 20 can extend through the arcuate slot 38 in the distal end 30 of the neck 12 and protrude into the head opening 42. As noted above, the brush shaft 14 may be disposed within the hollow interior of the neck 12. In this position, the tip of the axial extension 70 may abut the distal end of the axial receptacle 36 to form a first bearing surface. The ring 68 may abut the bearing surface 44 within the neck 12 to form a second bearing surface. Referring to FIG. 14, when the sleeve 48 is inserted and retained in the proximal end 28 of the neck, the second end 52 of the sleeve may abut the shaft end 62 of the brush shaft 14 to retain the brush shaft 14 in place. The brush shaft 14 may be formed from a single unitary piece of material, such as by injection molding the brush shaft 14 from the plastics noted above with respect to the neck 12.

Figure 9A:
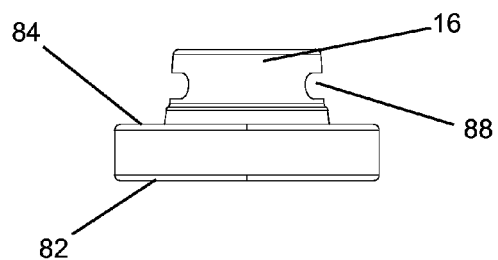
FIG. 9a is a front view of the bristle carrier.
Figure 9B:
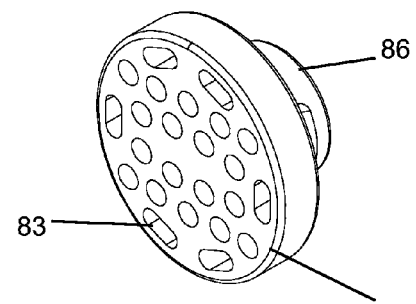
FIG. 9b is a perspective view of the bristle carrier.
Figure 9:
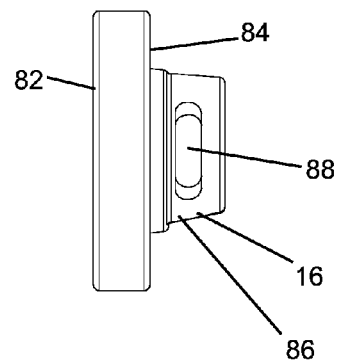
FIG. 9 is a side view of the bristle carrier.
Figure 8:
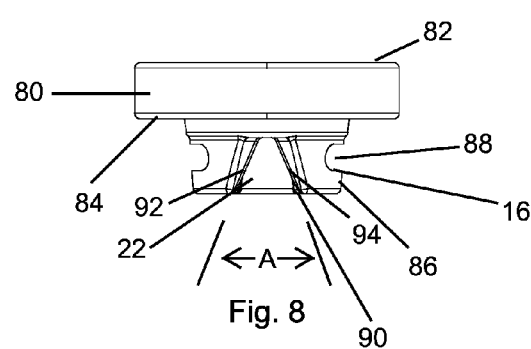
FIG. 8 is a rear view of a bristle carrier according to one embodiment.
Figures 10, 11:
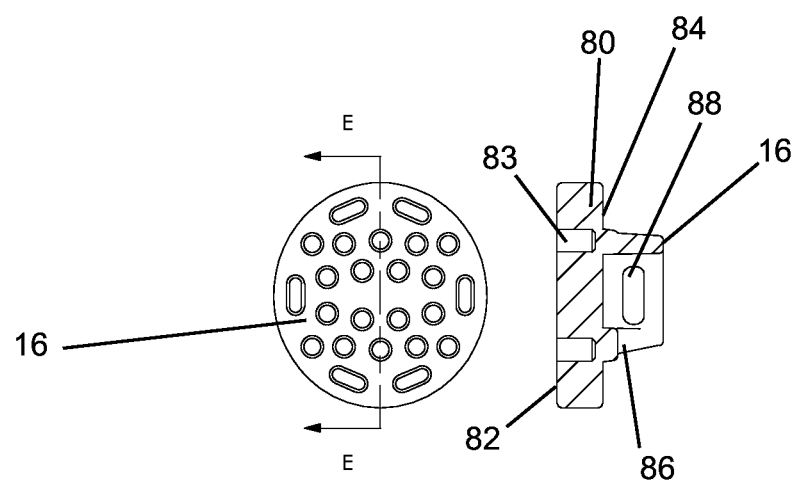
FIG. 10 is a top view of the bristle carrier.
FIG. 11 is a side cross-sectional view taken along line E-E in FIG. 10.

FIGS. 8-11 show the bristle carrier 16 in detail. Referring to FIG. 8, the bristle carrier 16 generally includes a cylindrical plate 80 having an upper bristle surface 82 and a lower surface 84. The bristle surface 82 may include a series of cleaning element holes 83 for receiving cleaning elements 85 such as bristles, elastomeric cleaning elements, or a combination thereof. When assembled, the lower surface 84 faces the rim 32 of the head 18. As shown in FIGS. 8 and 9, a protrusion 86 projects downwardly from the lower surface 84. The protrusion 86 may be generally cylindrical and may define an angled opening 22 as well as a pin slot 88. The angled opening 22 and the pin slot 88 may extend perpendicular to one another. In one embodiment, the angled opening may have a V-shape that widens as it approaches the lower surface 90 of the protrusion 86. The angle A between a first side 92 of the angled opening and a second side 94 may be controlled to provide the bristle carrier 16 with a desired amount of angular movement and to ensure that the eccentric extension 20 maintains contact with the angled opening 22 (at least contacting one of the sides 92, 94) at all times throughout the range of motion of the bristle carrier 16. In the illustrated embodiment, the angle is about 47 degrees. In an alternatively embodiment, the angle may be between about 20 and 60 degrees depending on the desired range of angular movement of the bristle carrier 16.

Also as shown in FIGS. 8 and 9 and FIG. 14, the pin slot 88 is sized to receive the retention pin 24, and is provided with a width greater than the diameter of the retention pin 24 such that the bristle carrier 16 can rotate through a degree of angular movement with the retention pin 24 extending completely through the pin slot 88. In the illustrated embodiment, the head includes opposing retention pin holes 100 for receiving the retention pin 24. The retention pins may be aligned along an axis that is transverse to the longitudinal axis of the brush head and transverse to the rotation axis of the bristle carrier 16. In one embodiment, the diameter of the retention pin 24 is about 0.05 mm, the height of the pin slot 88 is about the same (0.05 mm) and the width of the pin slot 88 is about 0.15 mm. As illustrated, the entrance of the pin slot 88 is chamfered, such that it tapers from an initial width of about 0.20 mm to the nominal width of about 0.15 mm. Although these dimensions provide a desired amount of movement of the pin 24 within the slot 88 in the illustrated embodiment, they may be varied from application to application. The pin may be constructed of a rigid material such as stainless steel. In one embodiment, the pin is made from SUS303 grade stainless steel to provide a desired retention strength.

When the bristle carrier 16 is assembled on the head 18, the lower surface 84 of the bristle plate 88 faces the rim 32 of the head, with the protrusion 86 of the bristle carrier 16 extending into the head opening 42 and spaced above the floor 34 of the head. The bristle carrier 16 is aligned as shown in FIGS. 1 and 14, with the pin slot 88 aligned generally along the pin axis and the angled opening 22 aligned along the longitudinal axis 26. The pin 24 is inserted through the retention pin holes 100 and through the pin slot 88 to retain the bristle carrier 16 on the head 18, while enabling a degree of angular movement between the bristle carrier 16 and the head 18. In addition, the eccentric extension 20 of the brush shaft 14 extends through the arcuate slot 38, into the head opening 42, and into the angled opening 22 of the bristle carrier 16.

C. Operation

In operation, the brush head 10 is plugged onto an electric toothbrush drive unit, with the sleeve 48 or neck 12 in mating engagement with a portion of the drive unit. In one example, the mounting structure 54 within the sleeve 48 interfits with the drive unit to prevent rotation of the brush head 10 with respect to the drive unit. The sleeve 48 may also form a friction fit with the drive unit to retain the brush head 10 on the drive unit. A drive shaft extends from the drive unit through the sleeve 48 and into the shaft opening 66 at the shaft end 62 of the brush shaft 14. The drive shaft and shaft opening may be shaped to fit interfit with one another to prevent rotation or movement of the brush shaft 14 with respect to the drive shaft. Rotational oscillation of the drive shaft thus translates into similar rotational oscillation of the brush shaft 14 about the longitudinal axis 26.

As the brush shaft 14 oscillates about the longitudinal axis 26, the axial extension 70 rotates within the axial receptacle 36 in the neck. The axial extension may include a dome shaped tip to enhance such rotation. The ring 68 on the main body of the brush shaft 14 may bear against the bearing surface 44 within the neck 12 and the interior surface of the neck 12 to prevent unwanted axial and lateral movement of the brush shaft 14. Furthermore, as the brush shaft rotates, the eccentric extension 20 oscillates back and forth within the arcuate slot 38 and within the angled opening 22 of the bristle carrier 16, causing the bristle carrier to rotate about a carrier axis that is perpendicular to the longitudinal axis of the brush head 10. The lower surface 84 of the bristle plate 80 rides on the upper rim 32 of the head, and the retention pin 24 extending through a retention pin holes 100 and the pin slot 88 in the bristle carrier retains the bristle carrier 16 on the head 18.

Referring now to FIGS. 15-20, one example of the angular rotation of the bristle carrier 16 is shown. FIGS. 15 and 16 show a bristle carrier 16 in a first angular position, wherein the brush shaft 14 is rotated to a position with the eccentric extension 20 located at the left side of the arcuate slot 38. This drives a clockwise rotation of the bristle carrier 16. FIGS. 17 and 18 show the brush shaft 14 rotated to a second, central position with the eccentric extension 20 positioned in the middle of the arcuate slot 38. With the brush shaft in this position, the bristle carrier 16 of FIG. 17 is shown in a central, or non-rotated, position. Finally, FIGS. 19 and 20 show the bristle carrier 16 in a third angular position, with the brush shaft 14 rotated so that the eccentric extension 20 is positioned at the right side of the arcuate slot 38. In this position, the eccentric extension 20, via its engagement with the V-shaped angled opening 22, drives the bristle carrier 16 to rotate angularly counterclockwise. In the illustrated embodiment, the arcuate slot 38 is sized to allow a pre-determined range of motion for the eccentric extension 20 (and thus the brush shaft 14). Referring to FIG. 20, the arcuate slot 38 may be sized to allow a range of motion to either side of the central position of about 28 degrees (see angle C). Thus the full range of motion of the brush shaft 14 (between the first and third angular positions) is about 56 degrees. This range of motion translates to the same range of motion of the bristle carrier 16 about the carrier axis (an axis extending out of the page in FIGS. 16, 18 and 20). As an example, FIG. 19 shows the bristle carrier 16 rotated to an angle B, which is about 28 degrees from the central position shown in FIG. 17. Thus, the bristle carrier also has a full range of motion of about 56 degrees. As noted above, although FIGS. 15-20 show one example of a desired range of motion of the bristle carrier 16, the width of the arcuate slot 38, the size of the eccentric extension 20 and the angle A of the V-shaped opening 22 may all be varied to alter the range of motion of the bristle carrier as desired.

Figure 21:
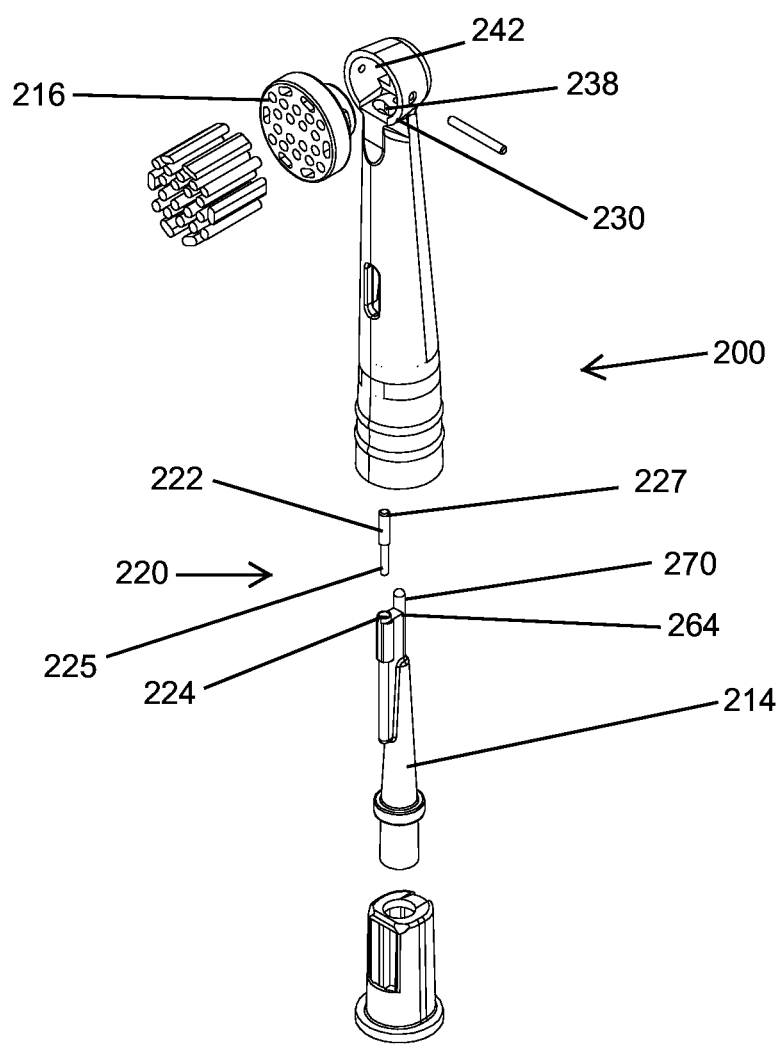
FIG. 21 is an exploded view of a brush head according to a second embodiment.
Figures 22, 23:
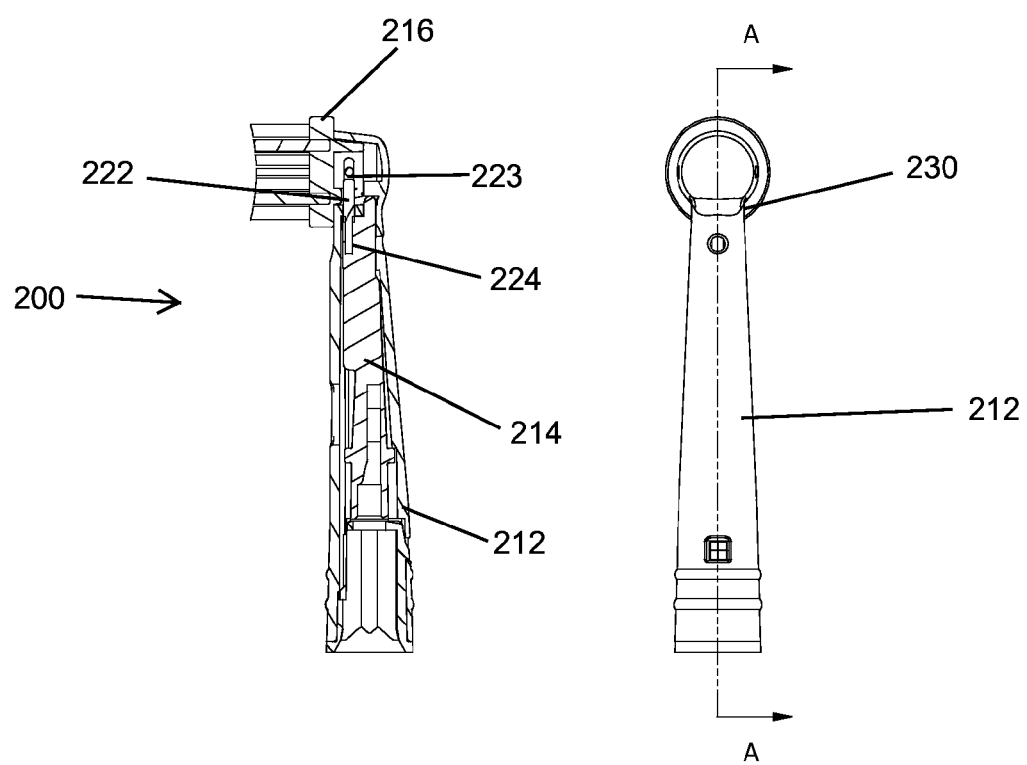
FIG. 22 is a rear view thereof.
FIG. 23 is a side cross-sectional view taken along line A-A in FIG. 22.

FIGS. 21-23 show an alternative embodiment of a replacement brush head 200, which is substantially the same as the brush head 10 described above, except that the eccentric extension 220 is formed with a rod 222 extending into a receptacle 224 on the brush shaft 214. In the illustrated embodiment, the rod 222 includes a portion 225 having a first diameter that extends into the receptacle 224 and a second portion 227 having a second diameter larger than the first diameter. The second portion extends outwardly from the end 264 of the brush shaft 214. The eccentric extension 220 extends from the head end 264 of the brush shaft 214 at an offset from the axial extension 270. As in the first embodiment, the amount of the offset may be varied as desired to control the amount of angular movement of the eccentric extension 220 and thus the distance of travel of the bristle carrier 216 during operation. In the illustrated embodiment, the eccentric extension 220 extends from the head end 264 a greater distance than the axial extension 270 such that the tip of the rod 222 can extend through the arcuate slot 238 in the distal end 230 of the neck 212 and protrude into the head opening 242. As the brush shaft 214 rotates, the eccentric extension 220 oscillates back and forth within the arcuate slot 238 and within the angled opening 223 of the bristle carrier 216, causing the bristle carrier 214 to rotate about a carrier axis that is perpendicular to the longitudinal axis of the brush head 200. In one embodiment, the rod 222 is fixed within the receptacle 224, such that the rod 222 does not rotate with respect to the receptacle 224. In another embodiment, the rod 222 may rotate within the receptacle as the brush shaft 214 is driven to rotate.

Figure 24:
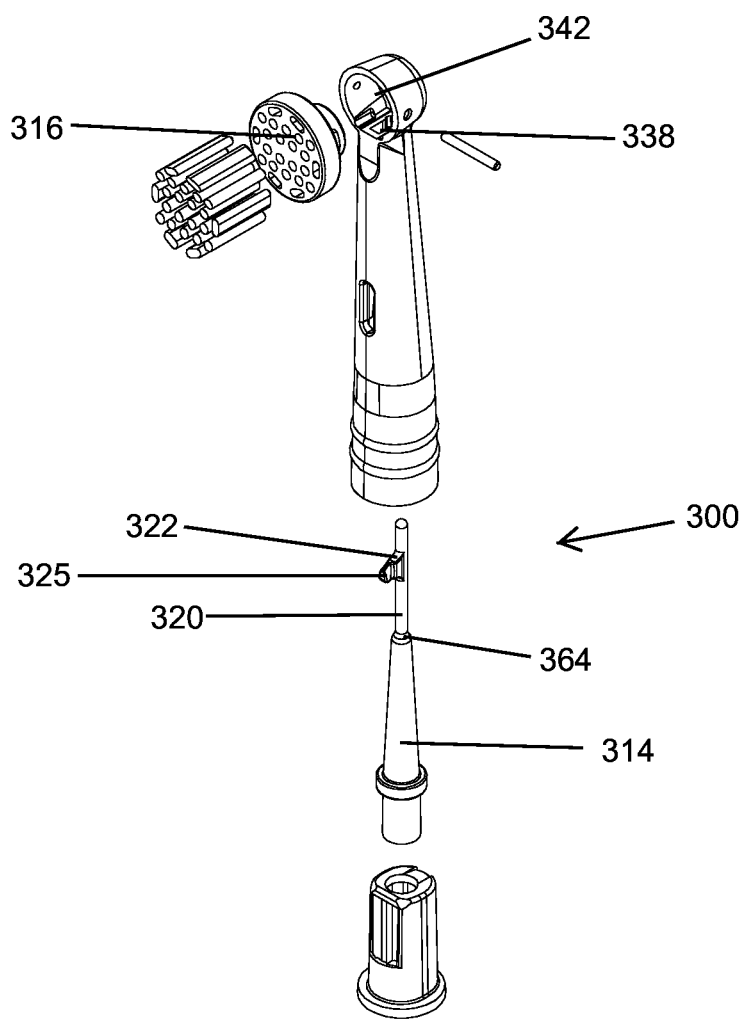
FIG. 24 is an exploded view of a brush head according to a third embodiment.

FIGS. 24-26 show an alternative embodiment of a replacement brush head 300. In this embodiment, a single extension portion 320 extends form the end 364 of the brush shaft 314 generally aligned with the longitudinal axis of the brush shaft 314. As illustrated, the extension portion 320 includes a bevel gear portion 322 extending outwardly therefrom in a direction generally perpendicular to the extension 320. In the illustrated embodiment, the bevel gear portion 322 includes gear teeth 325 that may interfit with corresponding gear teeth 327 on the bristle carrier 316. The bevel gear portion 322 extends from the extension 320 to a desired height. The height of the bevel gear portion 322 may be varied as desired to control the amount of angular movement of the bevel gear portion 322 and thus the distance of travel of the bristle carrier 316 during operation. In the illustrated embodiment, the extension 320 extends from the head end 364 a desired distance such that the tip of the extension 320 can extend through a hole 338 in the distal end 330 of the neck 312 and protrude into the head opening 342 and the gear teeth 325 interfit with the gear teeth 327 on the bristle carrier 316. As the brush shaft 314 rotates, the extension 320 oscillates about the longitudinal axis and within the hole 338 of the bristle carrier 316. The mating engagement of the teeth 225, 227 causes the bristle carrier 316 to rotate about the carrier axis that is perpendicular to the longitudinal axis of the brush head 300.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Additionally, any of the features from one embodiment may be used in another embodiment. Any reference to claim elements in the singular, for example, using the articles "a," "an," "the" or "said," is not to be construed as limiting the element to the singular.

The invention claimed is:
1. A replacement head for a toothbrush drive comprising:
   a tubular neck having a proximal end, a distal end opposite said proximal end and a head at said proximal end, said head including an upwardly opening sidewall, said sidewall defining a pair of opposing pin retention openings;
   a brush shaft disposed within said tubular neck, said brush shaft including a shaft end and a head end opposite said shaft end, said brush shaft defining a longitudinal axis, an eccentric extension extending from said head end and parallel with said longitudinal axis;
   a bristle carrier disposed on said head for rotation about a carrier axis transverse to said longitudinal axis, said bristle carrier defining a first opening receiving said eccentric extension therein, said bristle carrier defining a pin slot extending in a direction transverse to both said longitudinal axis and said carrier axis; and
   a pin extending through said pin retention openings and said pin slot to retain said bristle carrier on said head, wherein rotation of said brush shaft about said longitudinal axis causes rotation of said bristle carrier about said carrier axis.

2. The replacement head of claim 1 wherein said pin defines a diameter and said pin slot defines a height and a width, said height approximately the same as said diameter, said width greater than said diameter to enable rotation of said bristle carrier with respect to said pin.

3. The replacement head of claim 2 wherein said first opening in said bristle carrier is V-shaped.

4. The replacement head of claim 3 wherein said neck defines an arcuate slot in said distal end, said eccentric extension extending through said arcuate slot and into said first opening in said bristle carrier.

5. The replacement head of claim 4 wherein said bristle carrier includes a plate having an upper surface and a lower surface opposite said upper surface, a plurality of cleaning elements extending from said upper surface, and a protrusion extending from said lower surface and into said head, said first opening and said pin slot defined in said protrusion.

6. The replacement head of claim 5 wherein said pin slot extends in a direction perpendicular to said first opening.

7. The replacement head of claim 6 including an axial extension extending from said head end of said brush shaft parallel to said eccentric extension.

8. The replacement head of claim 7 wherein said brush shaft, eccentric extension and said axial extension are a single unitary piece.

9. The replacement head of claim 8 wherein said distal end of said neck defines an axial receptacle adjacent said arcuate slot, said axial extension extending into said axial receptacle.

10. A replacement head for an electric toothbrush comprising:
   a tubular neck having a proximal end, a distal end opposite said proximal end and a head at said proximal end, said head including an upwardly opening sidewall, said sidewall defining an arcuate slot;
   a brush shaft disposed within said tubular neck, said brush shaft including a shaft end and a head end opposite said shaft end, said brush shaft defining a longitudinal axis, said brush shaft including an eccentric extension extending from said head end through said arcuate slot, and an axial extension extending from said head end and parallel to said eccentric extension, said brush shaft capable of rotation about said longitudinal axis within a range of motion defined by said arcuate slot;
   a bristle carrier disposed on said head for rotation about a carrier axis transverse to said longitudinal axis, said bristle carrier defining a V-shaped opening receiving said eccentric extension therein; and
   wherein rotation of said brush shaft about said longitudinal axis causes rotation of said bristle carrier about said carrier axis, said eccentric extension engaging said V-shaped opening throughout said entire range of motion, and
   wherein said sidewall of said head defines opposing retention pin holes, and wherein said bristle carrier defines a pin slot extending in a direction transverse to both said longitudinal axis and said carrier axis, and
   wherein a pin extends through said retention pin holes and said pin slot to retain said bristle carrier on said head and permit rotation of said bristle carrier about said carrier axis.

11. The replacement head of claim 10 wherein said V-shaped opening defines an angle between about 20 and 60 degrees.

12. The replacement head of claim 11 wherein said V-shaped opening defines an angle between about 30 and 50 degrees.

13. The replacement head of claim 12 wherein said V-shaped opening defines an angle of about 46 degrees.

14. The replacement head of claim 10 wherein said pin defines a diameter and said pin slot defines a height and a width, said height approximately the same as said diameter, said width greater than said diameter to enable rotation of said bristle carrier with respect to said pin.

15. The replacement head of claim 14 wherein said bristle carrier includes a plate having an upper surface and a lower surface opposite said upper surface, a plurality of cleaning elements extending from said upper surface, and a protrusion extending from said lower surface and into said head, said first opening and said pin slot defined in said protrusion.

16. The replacement head of claim 15 wherein said brush shaft, eccentric extension and said axial extension are a single unitary piece.

17. The replacement head of claim 16 wherein said distal end of said neck defines an axial receptacle adjacent said arcuate slot, said axial extension extending into said axial receptacle.

18. A replacement head for an electric toothbrush comprising:
   a tubular neck having a proximal end, a distal end opposite said proximal end and a head at said proximal end, said head including an upwardly opening sidewall, said sidewall defining a pair of opposing pin retention openings, said distal end defining an arcuate slot and an axial receptacle, said arcuate slot extending through said distal end;
   a brush shaft disposed within said tubular neck, said brush shaft including a shaft end and a head end opposite said shaft end, said brush shaft defining a longitudinal axis, an eccentric extension extending from said head end and parallel with said longitudinal axis and an axial extension extending from said head end parallel to said eccentric extension, said eccentric extension extending through said arcuate slot, said axial extension extending into said axial receptacle;
   a bristle carrier disposed on said head for rotation about a carrier axis transverse to said longitudinal axis, said bristle carrier defining a V-shaped opening receiving said eccentric extension therein, said bristle carrier defining a pin slot extending in a direction transverse to both said longitudinal axis and said carrier axis; and
   a pin extending through said pin retention openings and said pin slot to retain said bristle carrier on said head, wherein rotation of said brush shaft about said longitudinal axis causes rotation of said bristle carrier about said carrier axis.

\* \* \* \* \*

UNITED STATES PATENT AND TRADEMARK OFFICE
CERTIFICATE OF CORRECTION

| | | |
|---|---|---|
| PATENT NO. | : 9,439,741 B2 | Page 1 of 1 |
| APPLICATION NO. | : 14/212020 | |
| DATED | : September 13, 2016 | |
| INVENTOR(S) | : Bryan J. Dishon | |

It is certified that error appears in the above-identified patent and that said Letters Patent is hereby corrected as shown below:

In the claims,
Column 8, Claim 1, lines 2-4:

"a tubular neck having a proximal end, a distal end opposite said proximal end and a head at said proximal end"

should be

--a tubular neck having a proximal end, a distal end opposite said proximal end and a head at said distal end--

Column 9, Claim 10, lines 3-5:

"a tubular neck having a proximal end, a distal end opposite said proximal end and a head at said proximal end"

should be

--a tubular neck having a proximal end, a distal end opposite said proximal end and a head at said distal end--

Column 10, Claim 18, lines 3-5:

"a tubular neck having a proximal end, a distal end opposite said proximal end and a head at said proximal end"

should be

--a tubular neck having a proximal end, a distal end opposite said proximal end and a head at said distal end--

Signed and Sealed this
Eighth Day of November, 2016

Michelle K. Lee
*Director of the United States Patent and Trademark Office*